United States Patent [19]

Chaiet et al.

[11] Patent Number: 4,670,466
[45] Date of Patent: Jun. 2, 1987

[54] R-(Z)-4-AMINO-3-CHLORO-2-PENTENEDIOIC ACID, NOVEL ANTIBACTERIAL AGENT

[75] Inventors: Louis Chaiet; Sheldon B. Zimmerman, both of Springfield; Richard L. Monaghan, Somerset, all of N.J.; Maria I. Martin, Madrid, Spain

[73] Assignee: Merck & Co., Inc., Rahway, N.J.

[21] Appl. No.: 778,118

[22] Filed: Sep. 20, 1985

Related U.S. Application Data

[60] Continuation-in-part of Ser. No. 719,067, Apr. 3, 1985, Pat. No. 4,600,691, which is a division of Ser. No. 541,174, Oct. 12, 1984, abandoned.

[51] Int. Cl.$^4$ .................. C07C 101/20; A01N 37/44
[52] U.S. Cl. .................... 514/547; 514/561; 514/626; 560/171; 562/571; 564/160
[58] Field of Search ............... 560/171; 562/574, 571; 564/160; 514/547, 561, 626

[56] References Cited

U.S. PATENT DOCUMENTS 3,528,995  9/1970  Mark .................................. 424/279

OTHER PUBLICATIONS

Chaiet, J. Antibiot, 37, pp. 207–210 (1984).
Roche, "Design of Biopharmaceutical Properties through Prodrugs and Analogs," pp. 281–315 (1977).
Kuroda, Y. J. Ant. 33: (3) 259–266, 1980.

*Primary Examiner*—Michael L. Shippen
*Attorney, Agent, or Firm*—Samuel B. Abrams; Hesna J. Pfeiffer

[57] ABSTRACT

R-(Z)-4-amino-3-chloro-2-pentenedioic acid is a novel antibacterial and isolated from *Streptomyces viridogenes* MA5450, ATCC 39387.

3 Claims, No Drawings

R-(Z)-4-AMINO-3-CHLORO-2-PENTENEDIOIC ACID, NOVEL ANTIBACTERIAL AGENT

This is a continuation in part of U.S. application Ser. No. 719,607 filed Apr. 3, 1985, now U.S. Pat. No. 4,600,691, which inturn is a division of application Ser. No. 541,174 filed Oct. 12, 1983, now abandoned.

BACKGROUND OF THE INVENTION

1. Field of the Invention

The present invention relates to a novel antibacterial compound, R-(Z)-4-amino-3-chloro-2-pentenedioic acid. The present invention encompasses the novel antibacterial in dilute forms, as crude concentrates, in pure forms, and in formulations suitable for antibiotic applications.

The novel compound R-(Z)-4-amino-3-chloro-2-pentenedioic acid is useful not only as an antibacterial agent, showing particular potency against Micrococcus luteus, but also as an intermediate for the preparation of known antibiotic FR-900148.

The present invention also relates to a process for preparing the novel antibacterial compound, R-(Z)-4-amino-3-chloro-2-pentenedioic acid, by fermentation of a nutrient medium with *Streptomyces viridogenes* MA5450, ATCC 39387.

The present invention further relates to a method of preparing known antibiotic FR-900148 by fermentation of a nutrient medium with *Streptomyces viridogenes* MA5450, ATCC 39387.

2. Brief Description of the Prior Art

*Streptomyles viridogenes* is a known species; Shirling, E. B. and D. Gottlieb, *Int. J. Syst. Bacteriol.* 16: 313–340, 1966. A new strain of this known species, MA5450, produces at least two antibacterial compounds. One is the novel antibacterial compound of the present invention, R-(Z)-4-amino-3-chloro-2-pentenedioic acid, and the other is a valine dipeptide of this compound, the known antibiotic FR-900148; Kuroda, Y., et al., *J. Antibiot.* 33 (3): 259–66, 1980.

BRIEF SUMMARY OF THE INVENTION

It is an object of the present invention to provide a new and useful antibiotic agent with antibacterial activity, namely, R-(Z)-4-amino-3-chloro-2-pentenedioic acid. It is another object of the present invention to provide a process for preparing the novel antibacterial agent, R-(Z)-4-amino-3-chloro-2-pentenedioic, by fermentation of a nutrient medium with *Streptomyces viridogenes* MA5450, ATCC 39387. It is a further object of the present inventio to provide a process for preparing the known antibiotic FR-900148, by fermentation of a nutrient medium with *Streptomyces viridogenes* MA5450, ATCC 39387.

DETAILED DESCRIPTION OF THE INVENTION AND PREFERRED EMBODIMENTS

In accordance with the present invention, there is provided an antibacterial compound of the formula:

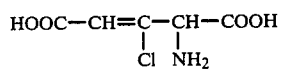

(I.)

and a pharmaceutically acceptable salt, ester, or amide thereof.

Antibacterial R-(Z)-4-amino-3-chloro-2-pentenedioic acid is obtained by growing under controlled conditions the microorganism, *Streptomyces viridogenes* MA5450, ATCC 39387 in a fermentation broth. The fermentation may be carried out in media containing suspended nutrient matter or in predominantly clear media wherein the medium is substantially free of suspended nutrient matter.

Based on extensive taxonomic studies, the antibiotic producing microorganism is identified as *Streptomyces viridogenes*. A useful strain is designated MA 5450 in the culture collection of MERCK & CO., Inc., Rahway, N.J. A culture thereof has been placed on permanent deposit with the culture collection of the American Type Culture Collection, 12301 Parklawn Drive, Rockville, Md. 20852, and has been assigned Accession No. ATCC 39387.

MORPHOLOGICAL AND CULTURAL CHARACTERISTICS OF *STREPTOMYCES VIRIDOGENES* MA5450, ATCC 39387

The morphological and cultural characteristics of *Streptomyces viridogenes* MA5450, ATCC 39387 are set forth below.

Morphology:

Morphological and cultural characteristics of the producing organisms were examined using standard media and procedures as described in Shirling E. B. and D. Gottlieb, *Int. J. Sept. Bacteriol.*, 16: 313–340, 1966. Based on comparison with the published description of known species of Streptomyces, it was determined that the producing organism is a new strain of a known species, identified in the Merck collection as *Streptomyces viridogenes* MA5450.

Cultural Characteristics of *Streptomyces viridogenes* MA5450, ATCC 39387

(V=vegetative growth; A=aerial mycelium; SP=soluble pigment)

Morphology: Sporophores are formed in tufts with flexuous to crooked chains of spores. Spores are spherical to oval, often cylindrical, $0.9 \times 1.2\mu$. Spore surface is smooth.

Oatmeal agar (ISP Medium 3)
  V: Rev. - dark gray-brown
  A: Dark brownish-gray (5fe) mixed with some white; powdery
  SP: Medium gray-brown
Czapek Dox agar (sucrose nitrate agar)
  V: Fair growth, light gray-brown
  A: Fair, light gray
  SP: Very light gray
Egg albumin agar
  V: Moderate; gray-brown
  A: Moderate; light gray
  SP: Light gray-brown
Glycerol asparagine agar (ISP Medium 5)
  V: Rev. - dark gray-brown
  A: Medium brownish gray (3fe) mixed with white. Powdery to grainy.
  SP: Light grayish-tan
Inorganic salts-starch agar (ISP Medium 4)
  V: Rev. - dark gray
  A: Medium brownish-gray (3fe) mixed with white. Powdery.

SP: Light gray
Yeast extract-malt extract agar (ISP Medium 2)
 V: Rev. - grayish brown
 A: Dark brownish gray mixed with medium gray and white (5fe).
 SP: Light grayish-brown.
Peptone-iron-yeast extract agar
 V: Tan
 A: None
 SP: None
 Melanin: Negative
Nutrient tyrosine agar
 V: Rev. - Dark gray
 A: Moderate, light gray
 SP: None
Tyrosine Agar (ISP Medium 7)
 V: Light gray
 A: Moderate, medium gray
 SP: Light grayish-tan
Carbon utilization
 Pridham-Gottlieb basal medium+1% carbon source;
 +=growth,;
 +=growth poor or questionable;
 −=no growth as compared to negative control (no carbon source)

| | |
|---|---|
| Glucose | + |
| Arabinose | + |
| Cellulose | − |
| Fructose | + |
| Inositol | + |
| Lactose | + |
| Maltose | + |
| Mannitol | + |
| Mannose | + |
| Raffinose | + |
| Rhamnose | − |
| Sucrose | ± |
| Xylose | + |

Temperature range (Yeast extract-dextrose +salts agar)
 28° C.—Good vegetative growth and good aerial growth with sporulation
 37° C.—No growth
 50° C.—No growth
Oxygen requirements (Stab culture in yeast extract-dextrose+salts agar)
 Aerobic All readings taken after three weeks at 28° C. unless noted otherwise. pH of all media approximately neutral (6.8–7.2).

Color number designations taken from Color Harmony Manual, 1958, 4th Edition, Container Corporation of America, Chicago, Ill.

PREPARATION OF
R-(Z)-4-AMINO-3-CHLORO-2-PENTENEDIOIC
ACID

The novel antibacterial compound of the present invention is produced during the aerobic fermentation of suitable aqueous nutrient media under controlled conditions via inoculation with the organism *Streptomyces viridogenes* MA5450, ATCC 39387. Aqueous media, such as those employed for the production of other antibiotics are suitable for producing the novel antibacterial compound of the present invention. Such media contain sources of carbon, nitrogen and inorganic salts assimilable by the microorganism. Many fermentation media support production of R-(Z)-4-amino-3-chloro-2-pentenedioc acid by *Streptomyces viridogenes* MA5450, ATCC 39387, and may be suitably adjusted within the ordinary skill of the fermentation chemist.

In general, carbohydrates, for example, dextrose and lactose and starches as well as glycerol, pectin and peptonized milk either alone or in combination can be used as sources of assimilable carbon in the nutrient medium. The exact quantity of the carbon source or sources utilized in the medium depends in part upon the other ingredients of the medium but, in general, the amount of carbon source usually varies between about 1% and 6% by weight of the medium. These carbon sources can be used individually or several such carbon sources can be combined in the medium.

Many proteinaceous materials may be used as nitrogen sources in the fermentation process. Suitable nitrogen sources include, for example, yeast extract, yeast hydrolysates, soybean flour, distillers solubles, corn steep, peptonized milk, lard water, peanut meal and tomato paste and the like. The sources of nitrogen, either alone or in combination, are used in amounts ranging from about 0.2% to 6% by weight of the aqueous medium.

Among the nutrient inorganic salts which may be incorporated in the medium are the customary salts capable of yielding sodium, potassium, ammonium, calcium, magnesium, phosphate, sulfate, chloride, carbonate and the like ions. Also, there may be included trace metals such as cobalt, manganese and iron.

The fermentation is carried out at temperatures ranging from about 20° C. to 37° C.; however, for optimum results it is preferred to conduct the fermentation at temperatures of from about 24° C. to 32° C. The pH of the nutrient media suitable for growing *Streptomyces viridogenes* MA5450, ATCC 39387 culture and producing the novel antibacterial compound of the present invention should be in the range of from about 4.0 to 7.0.

Small scale fermentation of the antibiotic conveniently is carried out by inoculating a suitable nutrient medium with the antibiotic-producing culture and, after transfer to a production medium, permitting fermentation to proceed at a constant temperature of about 28° C. on a shaker for several days. At the end of the incubation period, the antibiotic activity is isolated from the fermentation broth by techniques hereinafter described.

The small scale fermentation may be conducted in a sterilized flask via a one, two, three or four-stage seed development. The nutrient medium for the seed stage may be any suitable combination of carbon and nitrogen sources. The seed flask is shaken in a constant temperature chamber at about 28° C. until maximum growth is completed (usually 1–3 days) and some of the resulting growth is used to inoculate either a further seed-stage or the production medium. Intermediate stage seed-flasks, when used, are developed essentially in the same manner; that is, part of the contents of the flask is used to inoculate either the next stage seed medium or the production medium. The inoculated production flasks are shaken at a constant temperature (about 28° C.) for several days (usually 3 to 5 days) and at the end of the incubation period the novel antibacterial compound of the present invention is isolated.

For large scale work, it is preferable to conduct the fermentation in suitable tanks provided with an agitator and a means of aerating the fermentation medium. The nutrient medium is made up in the tank and sterilized by heating to about 120° C. Upon cooling, the sterilized medium is inoculated with a previously grown seed culture of the producing organism and fermentation is permitted to proceed for a period of several days (3 to 5 days, for example) while agitating and/or aerating the nutrient medium and maintaining the temperature at about 28° C.

EXAMPLE 1

Fermentation Preparation of R-(Z)-4-amino-3-chloro-2-pentenedioic acid

As in the case with most Streptomyces antibiotic fermentations, more than one antibiotic can be produced by *Streptomyces viridogenes* MA5450, ATCC 39387. Fermentation, therefore, attempted to maximize production of the desired antibiotic while minimizing the production of interfering antibiotics.

Enriched production of 4-amino-3-chloro-2-pentenedioic acid occured when the above culture was inoculated into growth medium A, Table I below, incubated for 2 days at 28° C. with agitation and then used to inoculate (5% inoculum) flasks containing production medium B, Table I below. Product was present after 24 hours of incubation. Fermentations were complete by 5 days of incubation at 28° C. with agitation.

The cell wall active compound FR-900148 was enriched when the above growth medium was used to inoculate production medium C, Table I below, which was allowed to incubate for 2 days at 28° C. with agitation.

The most consistent production of the antibiotic mixture occurred in production medium D, Table I below, under similar incubation conditions.

TABLE I

| Ingredient (g/l) | Composition of Media | | | |
| --- | --- | --- | --- | --- |
| | Medium A | Medium B | Medium C | Medium D |
| Dextrose | 1.0 | 45.0 | 20.0 | |
| Soluble Starch | 10.0 | | | |
| Corn Meal | | | | 10.0 |
| Beef Extract | 3.0 | | | |
| Yeast Autolysate (Ardamine pH) | 5.0 | 2.5 | | 5.0 |
| Peptone (NZ Amine E) | 5.0 | | | |
| Peptonized Milk | | 24.0 | | |
| Cottonseed Meal (Pharmamedia) | | | 6.0 | |
| Tomato Paste | | | | 30.0 |
| (NH4)2SO4 | | | 4.0 | |
| KH2PO4 | 0.182 | | | |
| Na2HPO4 | 0.190 | | | |
| MgSO4.7H2O | 0.05 | | | |
| CaCO3 | 0.5 | | 8.0 | |
| ZnSO4.7H2O | | | | |
| FeSO4.7H2O | | | | |
| Polyglycol P2000 | | 2.5 ml | | |
| pH | 7–7.2 | 7.0 | 7.0 | 5.0 |

EXAMPLE 2

Isolation of R-(Z)-4-amino-3-chloro-2-pentenedioic acid and FR-900148

A. R-(Z)-4-Amino-3-chloro-2-pentenedioic acid

The purification procedure to isolate the title compounds may be illustrated as follows:

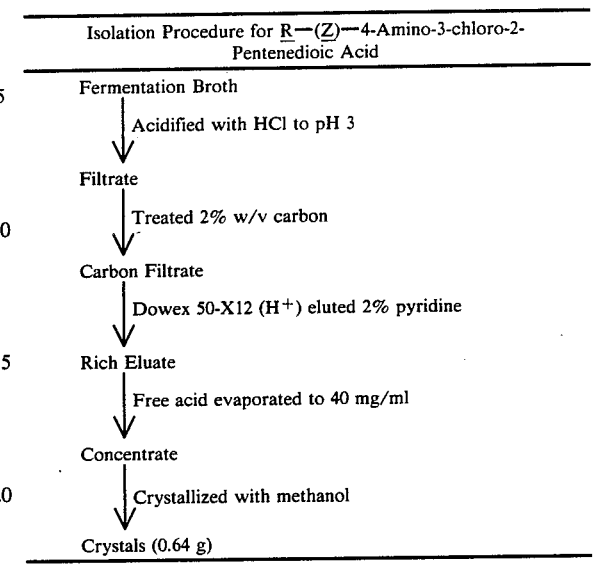

The fermentation broth (13 liters) was adjusted to pH 3.0 with 2.5 N HCl and filtered. The filtrate (121 g solids) contained both *Bacillus subtilis* and *Micrococcus luteus* activity and was treated with 250 g activated carbon. The slurry was filtered. Most of the Micrococcus activity was in the carbon filtrate whereas the Bacillus activity was reduced by one-half. The filtrate was passed through an 800 ml Dowex 50-X12 (H+ cycle) column followed by one liter of water. The resin spent effluent was devoid of bioactivity. The resin was eluted with 10 liters of 2% pyridine and one liter fractions were taken. The initial eluate fractions were at pH 3.0 and contained only the Micrococcus activity. The four highest activity fractions were combined and evaporated to 50 ml (1.7 g solids). An equal volume of methanol was added and the mixture allowed to set in the refrigerator for 16 hours. The crystals formed were filtered and dried to yield 643 mg of product. THe crystals were subjected to $^1$H-nmr studies.

Forty mg of crystals were dissolved in one ml H2O, heated and allowed to cool to room temperature to initiate large crystal formation. The solution was then put in the refrigerator for 72 hours. The large crystals formed were evaluated by X-ray crystallography.

B. FR-900148

FR-900148 was also isolated. The isolation was monitored by both *Bacillus subtilis* and *Micrococcus luteus* agar diffusion assays. Fermentation broth was centrifuged. The clear liquid (900 ml, 19.8 g solids) was adjusted to pH 9.0 and passed through a 175 ml Dowex 1-X2 (Cl−) resin followed by 400 ml H2O. The absorbed antibiotic was eluted with 800 ml of 3% NaCl, taking 200 ml fractions. The active fractions were combined, adjusted to pH 7.0 and evaporated to 45 ml. The concentrate was treated with an equal volume of methanol to precipitate salt and the clear liquid was evaporated to 30 ml. Twenty ml of the concentrate was passed through a 900 ml Biogel P-2 column collecting 10 ml fractions. The first peak fraction (No. 54) contained an equal amount of Micrococcus and Bacillus activity (FR-900148) whereas the second peak contained increased amounts of Micrococcus activity (R-(Z)-4-amino-3-chloro-2-pentenedioic acid). Fraction No. 54 was freeze dried to yield 38 mg of product which was subjected to nmr analysis.

EXAMPLE 3

Physicochemical characterization of R-(Z)-4-amino-3-chloro-2-pentenedioic acid and FR-900148

A. R-(Z)-4-amino-3-chloro-2-pentenedioic acid

The crystals decomposed above 138° C. The antibacterial was not extracted from water with organic solvents.

Elemental analysis called for $C_5H_6NO_4Cl$: Calc'd: C, 33.42; H, 3.37; N, 7.80; Cl, 19.75; Found: C, 33.55; H, 3.38; N, 7.70; Cl, 19.24.

The H-nmr spectrum on a Varian SC300 showed only two peaks in $D_2O$ (two drops of DCl added) with the following characteristics: $\delta 5.17$ (1H, s) and $\delta 6.80$ (1H, s) indicating a structure of:

$$HOOC-CH=C-CH-COOH$$
$$\quad\quad\quad\quad | \quad\; |$$
$$\quad\quad\quad\quad Cl \;\; NH_2$$

X-Ray Crystallography

FIG. 1 is a computer generated drawing of R-(Z)-4-amino-3-chloro-2-pentenedioic acid in which the structure was solved with the application of direct methods. (Main, P. MULTAN, a program for the automatic solution of crystal structures from X-ray diffraction data by multiple starting point tangent formula. University of York, England, 1980.) It shows the correct configuration at C4 of R which is analogous to the S configuration of L-amino acids. In addition, the X-ray experiments show that the configuration around the double bound is Z. As would be expected, the compound exists in a zwitterion form with the carboxyl protonated.

B. FR-900148

A $D_2O$ H-nmr spectrum using a Varian XL-200 showed the following characteristics for the title compound:

$\delta 1.06$ (3H, d, $J=7H_z$), $\delta 1.07$ (3H, d, $J=H_z$), $\delta \sim 2.3$ (1H, m), $\delta 3.96$ (1H, d, $J=6H_z$), $\delta 5.02$ (1H, s), $\delta 6.48$ (1H, s). These peaks are consistent to those reported for FR-900,148.

EXAMPLE 4

Biological Characteristics of R-(Z)-4-amino-3-chloro-2-pentenedioic acid

The activity of R-(Z)-4-amino-3-chloro-2-pentenedioic acid against *Micrococcus luteus* may be demonstrated by the following test. A set of Petri plates containing 5 ml of nutrient agar seeded with *Micrococcus luteus* are prepared. Filter discs (⅜ inch) containing R-(Z)-4-amino-3-chloro-2-pentenedioic acid at various concentrations are placed on the surface of the agar plates which are then incubated overnight at 37° C. Large zones of inhibition occur around the discs. Typical results are shown below.

| R—(Z)—4-amino-3-chloro-2-pentenedioic acid concentration | | Zone Diameter (mm: 3/8″ Disc) |
|---|---|---|
| μg/ml | μg/disc* | Micrococcus luteus |
| 1000 | 50 | 53 |
| 500 | 25 | 47 |
| 250 | 12.5 | 43 |
| 125 | 6.3 | 37 |
| 62.5 | 3.2 | 31 |
| 31.3 | 1.6 | 23 |
| 15.7 | 0.8 | 17 |
| 7.9 | 0.4 | 0 |

*50 lamda applied per disc

Antibacterial activity of R-(Z)-4-amino-3-chloro-2-pentenedioic acid against other gram positive microorganisms, particularly, species of Staphylococcus and Streptomyces, can be shown.

When used as an antibacterial, R-(Z)-4-amino-3-chloro-2-pentenedioic acid may be employed in the form of pharmaceutical preparations which contain it in admixture or conjunction with an organic or inorganic solid or liquid pharmaceutical excipient suitable for internal, parenteral or local administration. Suitable excipients are substances that do not react with the antibiotic, for example, water, gelatin, lactose, starches, stearyl alcohol, magnesium stearate, talcum, vegetable oils, benzyl alcohols, gums, propylene glycols, polyalkylene glycols, white petroleum jelly, cholesterol or other known pharmaceutical excipients. The pharmaceutical formulations may be, for example, tablets, dragees, ointments, creams or capsules, or in liquid form solutions, suspensions or emulsions. They may be sterilized and/or contain assistants such as preserving, stabilizing, wetting or emulsifying agents, solution promoters, salts for regulating osmotic pressure or buffers.

Where it is desired to administer the antibiotic in dry, solid unit dosage form, capsules, boluses or tablets containing the desired amount of antibiotic are employed. These dosage forms are prepared by intimately and uniformly mixing the active ingredient with suitable finely divided diluents, fillers, disintegrating agents and/or binders such as, for example, starch, lactose, talc, magnesium stearate, vegetable gums and the like. Such unit dosage formulations may be varied widely with respect to their total weight and content of antibacterial R-(Z)-4-amino-3-chloro-2-pentenedioic acid depending upon factors such as the type of host to be treated, the severity and type of infection to be treated and the weight of the host. Conveniently, the antibiotic may be administered on a daily basis at from about 5 to about 100 mg per kilogram of body weight.

EXAMPLE 5

$$\underset{1}{\overset{\displaystyle HOOC\quad H}{\underset{\displaystyle H_2N\quad COOH}{\overset{\displaystyle \diagdown \; \diagup}{\underset{\displaystyle \diagup \quad \diagdown}{Cl-\overset{\|}{\underset{|}{C}}\underset{CH}{}}}}}} \xrightarrow{\dfrac{SOCl_2}{CH_3OH}}$$

-continued

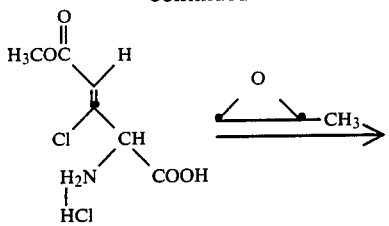

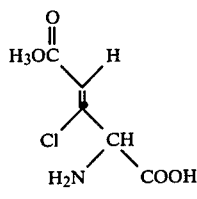
2

(L,Z) 3-Chloro-Δ-3-glutamic acid γ-monomethyl ester
2

(L,Z) 3-Chloro-Δ-3-glutamic acid 1 (720 mg, 4.00 mmol) was added in portions to a stirred solution at 0° of thienyl chloride (640 mg, 5.36 mmol) in 10 ml of methanol. The chloro-Δ-3-glutamic acid dissolved rapidly and the solution was kept at 0° to +5° for 96 hours at which time tlc indicated nearly complete conversion of starting material to a more mobile component. The mixture was concentrated to dryness, take up in methanol, charcoaled to remove color and redissolved in 10 ml of methanol. Propylene oxide (4 ml) was added and the mixture stirred one hour. Compound 2 precipitated and was filtered and washed with methanol (535 mg, 70%) m.p. 130°–135° dec.; tlc, silica gel ethylacetate:n-butanol:acetic acid:water-1:1:1:1, $R_f$=0.58; nmr (D$_2$O+DCl) δ3.65(s, OCH$_3$), 4.91(s, CαH), 6.58(s, CγH); ms (FAB) M+1=194,196.

EXAMPLE 6

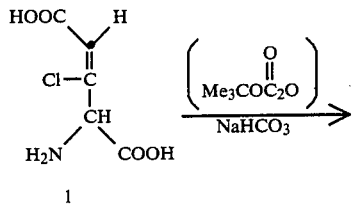
1

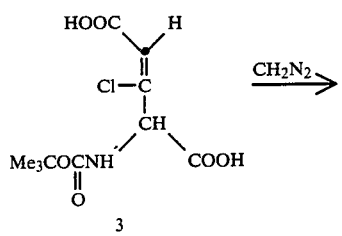
3

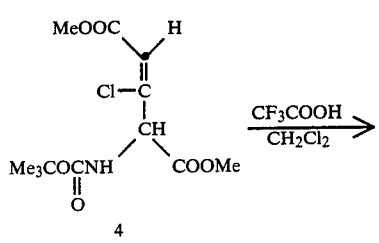
4

-continued

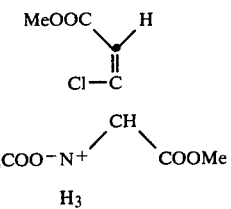
5

(L,Z) 3-Chloro-Δ-3-glutamic acid dimethyl ester trifluoracetate 5

To a stirred mixture of (L,Z)-3-chloro-Δ-3-glutamic acid (720 mg; 4 mmol) and di-tertbutyl dicarbonate (960 mg; 4.4 mmol) in water (28 ml) and tetrahydrofuran (28 ml) was added sodium bicarbonate (1.042 g; 12.4 mmol). The pale yellow solution was stirred 18 hours and concentrated on the water pump to remove tetrahydrofuran. The solution was extracted once with ethyl acetate, acidified with aqueous sodium bisulfate and extracted four times with ethyl acetate. The organic extract was dried over sodium sulfate and concentrated to dryness to give the t-butyoxycarbonyl derivative 3 (∼1.00 g).

To the latter in tetrahydrofuran (2 ml) and ether (4 ml) at 0° was added a cold ether solution of diazomethane until the color of free diazomethane was evident. The solution was concentrated to dryness to give the t-butoxycarboxyl dimethyl ester 4 (1.015 g).

To a stirred solution of 4 in 3 ml of methylene chloride at 0° was added 6 ml of chilled (0°) trifluoroacetic acid:methylene chloride-1:1. After 1 hour at 0° the mixture was concentrated to dryness to give the dimethylester trifluoroacetate 5 nmr (D$_2$O) δ3.68(s, OCH$_3$), 3.78(s, OCH$_3$), 5.10(s, CαH), 6.58(CγH).

Included within the scope of the present invention are the non-toxic, pharmaceutically acceptable salts of R-(Z)-4-amino-3-chloro-2-pentenedioic acid. Such salts include, for example, the alkali metal and alkaline earth metal salts such as those derived from sodium, potassium or calcium or salts derived from ammonium, or salts derived from organic bases such as triethylamine, N-ethylpiperidine, dibenzylethylenediamine and the like.

Also included within the scope of the present invention are the non-toxic, pharmaceutically acceptable esters and amides of R-(Z)-4-amino-3-chloro-2-pentenedioic acid. Such esters and amides are those which would readily occur to the skilled artisan, and include, for example, C$_{1-4}$ alkyl esters and amides of either or both carboxyl groups.

What is claimed is:
1. The compound:

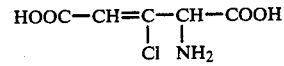

and pharmaceutically acceptable salts thereof.

2. A compound selected the C$_{1-4}$ alkyl esters and C$_{1-4}$ alkyl amides of either or both carboxyl groups of the compound having the general formula:

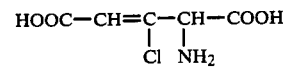

3. An antibacterial composition comprising an antibacterially effective amount of the compound of claim 1 or 2 and a pharmaceutically effective carrier.

* * * * *